(12) United States Patent
Takagi

(10) Patent No.: US 8,021,843 B2
(45) Date of Patent: Sep. 20, 2011

(54) BIOLOGICAL SAMPLE REACTION CHIP AND BIOLOGICAL SAMPLE REACTION METHOD

(75) Inventor: Fumio Takagi, Chino (JP)

(73) Assignee: Seiko Epson Corporation (JP)

( * ) Notice: Subject to any disclaimer, the term of this patent is extended or adjusted under 35 U.S.C. 154(b) by 248 days.

(21) Appl. No.: 12/260,179

(22) Filed: Oct. 29, 2008

(65) Prior Publication Data

US 2009/0123978 A1    May 14, 2009

(30) Foreign Application Priority Data

Nov. 8, 2007   (JP) .................................. 2007-291214

(51) Int. Cl.
*C12Q 1/68* (2006.01)
(52) U.S. Cl. ........................................................ 435/6.1
(58) Field of Classification Search ........................ None
See application file for complete search history.

(56) References Cited

U.S. PATENT DOCUMENTS

2003/0138941 A1 * 7/2003 Gong et al. ................. 435/287.2

FOREIGN PATENT DOCUMENTS

| JP | 2000-236876 | 9/2000 |
| JP | 2007-064742 | 3/2007 |
| JP | 2007-523355 | 8/2007 |
| JP | 2007-292714 | 11/2007 |

* cited by examiner

*Primary Examiner* — Christopher M. Babic
(74) *Attorney, Agent, or Firm* — Harness, Dickey & Pierce, P.L.C.

(57) ABSTRACT

A biological sample reaction chip, including: a plurality of reaction vessels; a first channel connected to one end of each of the reaction vessels and comprising an opening for introducing a reaction solution; and a second channel connected to the other end of each of the reaction vessels, wherein when a capillary force of the first channel is defined as A, while a capillary force of connected portions between the reaction vessels and the first channel as B, a capillary force of the reaction vessels as C, a capillary force of connected portions of the second channel and the reaction vessels as D, and a capillary force of the second channel as E, the following is established: A<B<C<D and E<D.

11 Claims, 3 Drawing Sheets

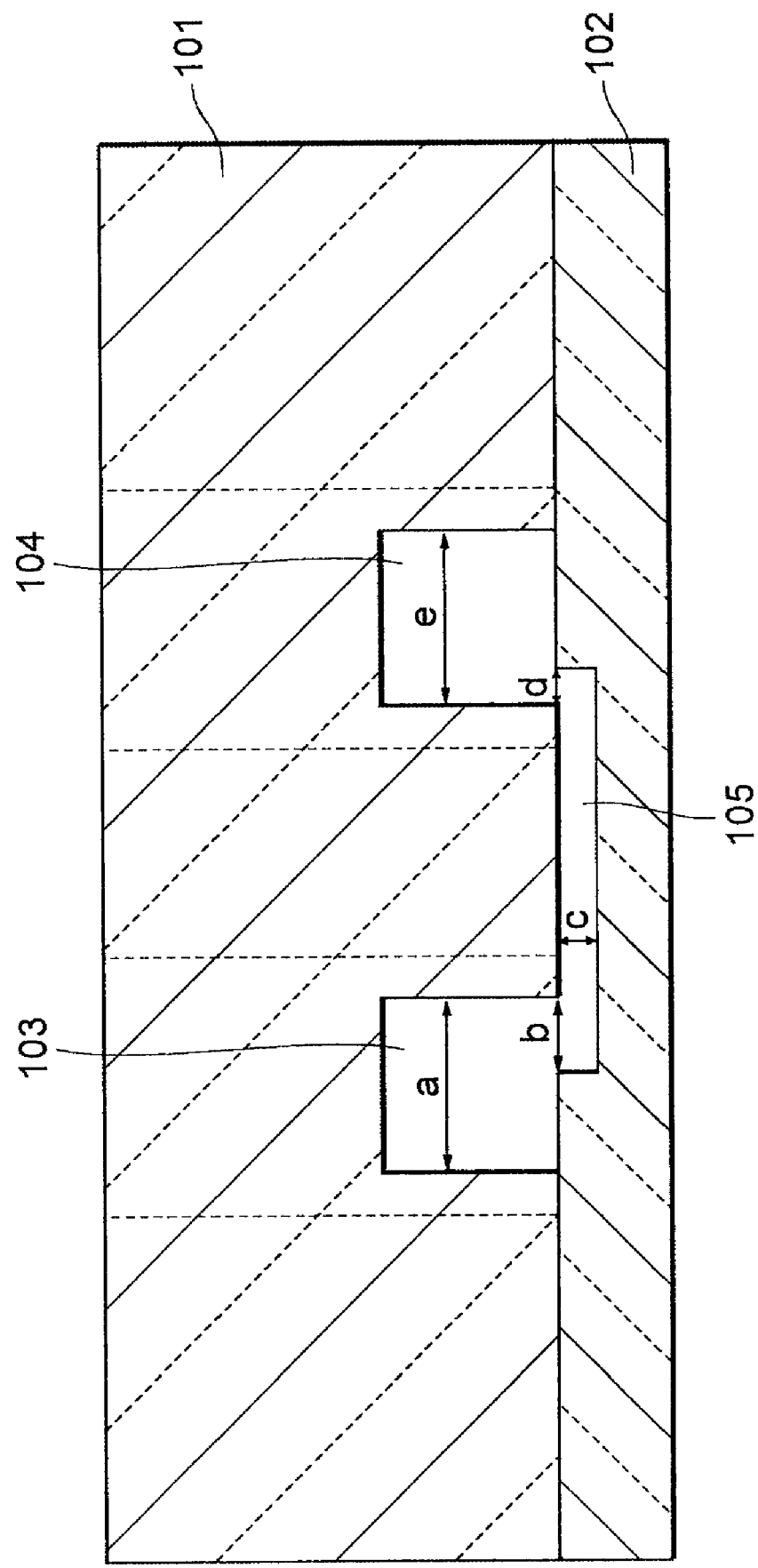

BIOLOGICAL SAMPLE REACTION CHIP AND BIOLOGICAL SAMPLE REACTION METHOD

CROSS-REFERENCE TO RELATED APPLICATIONS

This application relates to and claims priority from Japanese Patent Application No. 2007-291214, filed on Nov. 8, 2007, the entire disclosure of which is incorporated herein by reference.

BACKGROUND

1. Technical Field

The present invention relates to a biological sample reaction chip and a biological sample reaction method for performing biological sample reactions such as nucleic acid amplification.

2. Related Art

One method that has come to the forefront involves using a microfluid chip, in which a fine channel is provided to a glass plate or the like, to perform chemical analysis, chemical synthesis, bio-related analysis, and the like. These microfluid chips are also called micro total analytical systems (micro TAS), lab-on-a-chip, and so on, the advantages to which are that less sample or reagent is required than with conventional devices, the reaction time is shorter, there is less waste, and so forth, and these chips are expected to find use in a wide range of fields, such as medical diagnosis, on-site analysis of environments and foods, and the production of drugs, chemicals, and the like. Since a smaller amount of reagent may be used, the cost of testing can be reduced, and because the amount of sample and reagent is smaller, the reaction time is also much shorter, so the testing is more efficient. Particularly when these chips are used for medical diagnosis, since less blood or other specimen that serves as the sample is required, another advantage is that it reduces the burden on the patient.

The polymerase chain reaction (PCR) method is well known as a way to amplify the genes of DNA, RNA, and the like used as reagents and samples. PCR involves putting a mixture of the target DNA and a reagent into a tube, and repeatedly reacting the mixture with a temperature control apparatus called a thermal cycler, with temperature changes in three stages of 55° C., 72° C., and 94° C. repeated at a cycle of a few minutes. The action of the enzyme polymerase allows the target DNA to be amplified by approximately 2 times per temperature cycle.

A method called real time PCR, in which a special fluorescent probe is used, has become practical in recent years, and allows DNA to be quantified while performing an amplification reaction. Since real time PCR affords high measurement accuracy and reliability, it has come to be widely used for research and clinical testing purposes.

With a conventional device, however, the amount of reaction solution needed for PCR is typically a few dozen microliters, and a problem is that basically only one gene can be measured with a single reaction system. With another method, about four different genes can be measured simultaneously by using a plurality of fluorescent probes and differentiating by color, but the only way to simultaneously measure more genes than this is to increase the number of reaction systems. The amount of DNA extracted from a specimen is generally very small, and reagents are expensive, so measuring many reaction systems at the same time is problematic.

JP-A-2000-236876 discloses a method in which integrated microwells are produced on a semiconductor substrate, and PCR is conducted in these wells, allowing many different DNA samples to be amplified and analyzed at the same time using only tiny amounts of sample.

However, JP-A-2000-236876 does not disclose a specific method for introducing a tiny amount of sample into a well. Actually, it was very difficult in the past to quantify a tiny amount (1 μL or less) of reaction solution and efficiently supply it to a reaction vessel.

SUMMARY

It is an object of the present invention to provide a biological sample reaction chip and a biological sample reaction method with which a small amount of reaction solution is supplied to a reaction vessel by an easy method, and efficient reaction processing can be carried out.

The biological sample reaction chip pertaining to the present invention has a plurality of reaction vessels, a first channel connected to one end of each of the reaction vessels and having an opening for introducing a reaction solution, and a second channel connected to the other end of each of the reaction vessels, wherein when a capillary force of the first channel is defined as A, while a capillary force of connected portions between the reaction vessels and the first channel as B, a capillary force of the reaction vessels as C, a capillary force of connected portions of the second channel and the reaction vessels as D, and a capillary force of the second channel as E the following is established: $A<B<C<D$ and $E<D$.

With the present invention, reaction vessels can be filled with a reaction solution by using capillary force, so an extremely small amount of reaction solution, which is difficult to quantify with a pipette, can be supplied in the specified amount to a reaction vessel. Thus, a small amount of reaction solution is supplied to reaction vessel by an easy method, and reaction processing can be carried out efficiently. Also, since only a small amount of reaction solution is needed, the cost can be reduced, and the reaction time is also greatly shortened, affording more efficient processing. Also, since processing can be performed in many reaction vessels at once, tests involving many different samples and so forth can be carried out efficiently with a small amount of reagent.

Each of the reaction vessels can be coated with a reagent necessary for a reaction. This allows the user to perform tests, etc., easily merely by filling reaction vessels.

The biological sample reaction method pertaining to the present invention is a biological sample reaction method that utilizes the above-mentioned biological sample reaction chip, having a step of supplying the reaction solution through the opening into the first channel and filling the reaction vessels with the reaction solution, a step of filling the first channel and the second channel with a liquid that is immiscible with the reaction solution and evaporates more slowly than the reaction solution, and a step of carrying out biological sample reaction processing.

With the present invention, since reaction vessels filled with a reaction solution by capillary force, an extremely small amount of reaction solution, which is difficult to quantify with a pipette, can be supplied in the specified amount to a reaction vessel. Thus, a small amount of reaction solution is supplied to reaction vessel by an easy method, and reaction processing can be carried out efficiently. Also, since only a small amount of reaction solution is needed, the cost can be reduced, and the reaction time is also greatly shortened, affording more efficient processing. Also, since processing can be performed in many reaction vessels at once, tests involving many different samples and so forth can be carried out efficiently with a small amount of reagent.

Furthermore, since a first channel and a second channel are filled with a liquid that that is immiscible with the reaction solution and evaporates more slowly than the reaction solution, the individual reaction vessels are separated, preventing contamination between reaction vessels. The reaction solution can also be prevented from evaporating during reaction processing.

Also, the biological sample reaction processing is processing that includes nucleic acid amplification, the reaction solution includes a target nucleic acid, an enzyme for amplifying a nucleic acid, and a nucleotide at a specific concentration of, and the reaction vessels can be coated ahead of time with a primer.

When real time PCR processing is performed, the inside of the reaction apparatus may be coated with a fluorescent probe ahead of time.

BRIEF DESCRIPTION OF THE DRAWINGS

FIG. 2 is a schematic diagram illustrating the size relationship of the various components of the microreactor array in Embodiment 1.

DESCRIPTION OF EXEMPLARY EMBODIMENTS

Embodiments of the present invention will now be described through reference to the drawings.

Embodiment 1

Figure 1A:
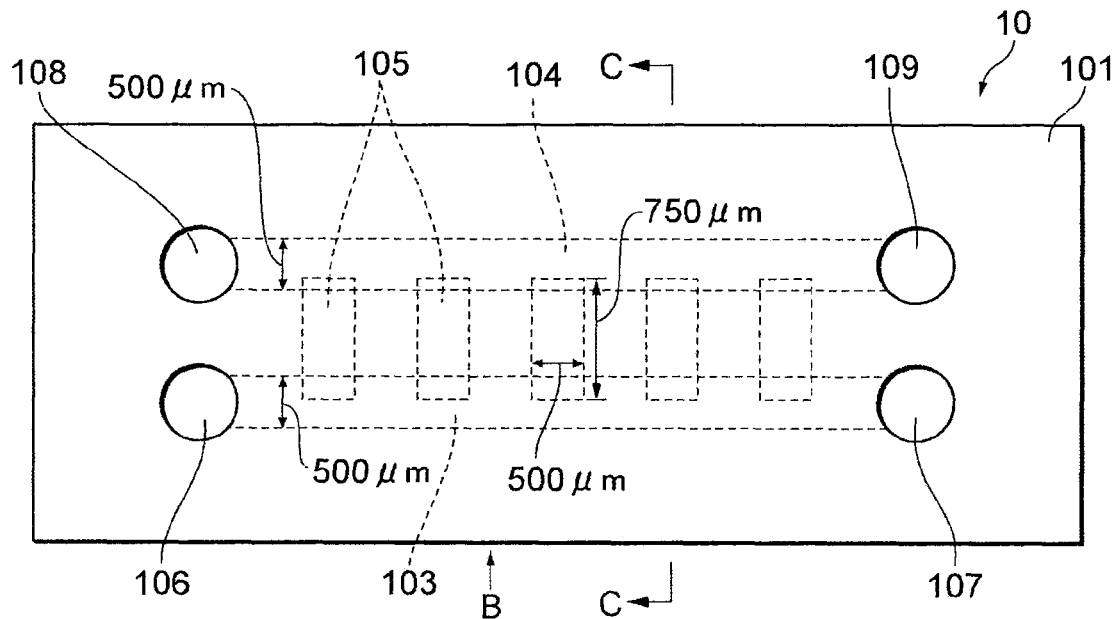
FIG. 1A is a top view illustrating the simplified configuration of a microreactor array pertaining to Embodiment 1 of the present invention.
Figure 1B:
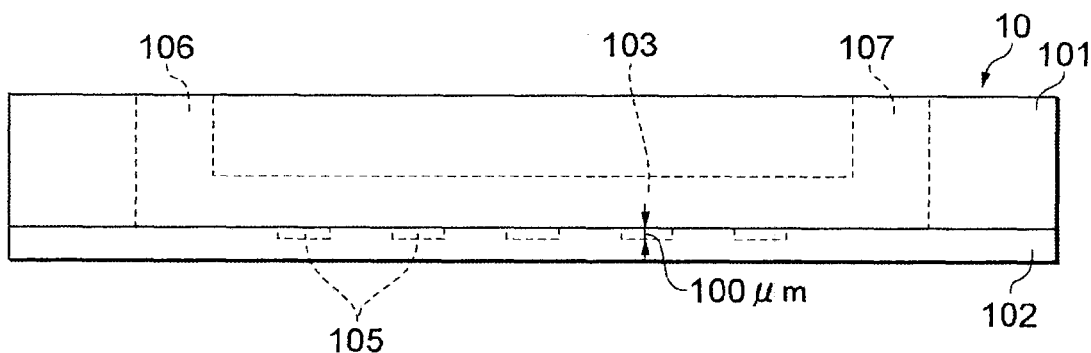
FIG. 1B is a front view of the microreactor array as seen in the direction B indicated in FIG. 1A.
Figure 1C:
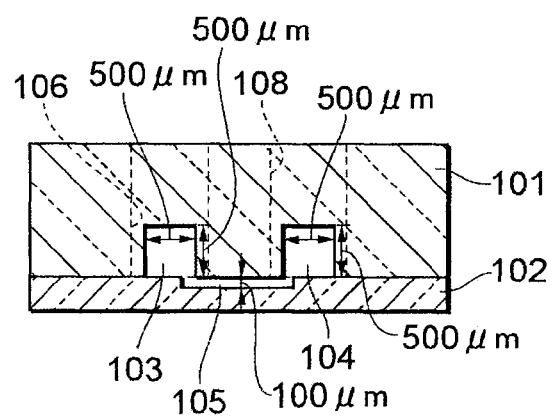
FIG. 1C is a cross section along the C-C line in FIG. 1A.

FIG. 1A is a top view illustrating the simplified configuration of a microreactor array (biological sample reaction chip) 10 pertaining to Embodiment 1 of the present invention. FIG. 1B is a front view of the microreactor array 10 as seen in the direction B indicated in FIG. 1A. FIG. 1C is a cross section along the C-C line in FIG. 1A. As shown in the drawings, a nucleic acid detector 10 [sic] has transparent base plates 101 and 102, a reaction solution introduction channel (first channel) 103, a discharge channel (second channel) 104, reaction vessels 105, and openings 106 to 109.

As shown in FIG. 1, the microreactor array 10 is constituted by affixing together the transparent base plates 101 and 102. In the transparent base plate 101 are formed the reaction solution introduction channel 103, the discharge channel 104, and the openings 106 to 109. The openings 106 and 107 are each connected to an end of the reaction solution introduction channel 103. As shown in FIG. 1, the reaction solution introduction channel 103 and the discharge channel 104 are formed in a width of 500 µm and a depth of 500 µm.

A plurality of reaction vessels 105 are formed in the transparent base plate 102. The reaction vessels 105 are formed in a size of 500×750 µm, and to a depth of 100 µm. The reaction vessels 105 are formed so that the reaction solution introduction channel 103 communicates with the discharge channel 104. The distance between adjacent reaction vessels 105 is set wide enough to prevent the mixing of reaction solution between reaction vessels 105.

The transparent base plates 101 and 102 can be glass plates, for example, in which case the reaction solution introduction channel 103, the discharge channel 104, the openings 106 to 109, and the reaction vessels 105 can be formed by etching or sandblasting.

The inner walls of the reaction vessels 105 are preferably given a lyophilic surface treatment, and the inner walls of the reaction solution introduction channel 103 and the discharge channel 104 are preferably given a lyophobic surface treatment. Moreover, the reaction solution introduction channel 103 and the inner walls of the reaction vessels 105 are preferably subjected to a surface treatment for suppressing nonspecific absorption of biomolecule of protein, for example.

FIG. 2 is a schematic diagram illustrating the size relationship of the various components of the microreactor array 10. FIG. 2 is a cross section along the C-C line in FIG. 1A. As shown in this drawing, if we let a be the width of the reaction solution introduction channel 103, b be the width of the connected portions of the reaction vessels 105 and the reaction solution introduction channel 103, c be the depth of the reaction vessels 105, d be the width of the connected portions of the discharge channel 104 and the reaction vessels 105, and e be the width of the discharge channel 104, the following relationships are satisfied.

$$a > b > c > d$$

$$e > d$$

In general, when a liquid moves into a slender channel, a capillary force P expressed by the following equation is exerted.

$$P = (l\gamma \cos \theta)/S$$

Here, l is the peripheral length of a cross section perpendicular to the flow of a channel, S is the surface area thereof, γ is the surface tension, and θ is the contact angle. γ and θ here are constant, and the width of the channel other than a to e is constant at 500 µm, so if we let A be the capillary force of the reaction solution introduction channel 103, B be the capillary force of the connected portions between the reaction vessels 105 and the reaction solution introduction channel 103, C be the capillary force of the reaction vessels 105, D be the capillary force of the connected portions of the discharge channel 104 and the reaction vessels 105, and E be the capillary force of the discharge channel 104, the following relationships are satisfied.

$$A < B < C < D$$

$$E < D$$

The method for supplying a reaction solution to the microreactor array 10 will be described through reference to FIG. 3A, FIG. 3B, FIG. 3C, and FIG. 3D. The reaction solution includes a target nucleic acid, a polymerase, and a nucleotide (dNTP) in a specific concentration that is suited to the reaction.

The target nucleic acid can be, for example, DNA extracted from a biological sample such as blood, urine, saliva, or cerebrospinal fluid, or cDNA that has been reverse transcripted from extracted RNA.

The reaction solution may also include a primer, but with the microreactor array in this working example, the inside of each of the reaction vessels 105 has been precoated with a primer and dried. Each of the reaction vessels 105 is coated with a different primer, allowing many PCRs to be conducted at the same time.

Figure 3D:
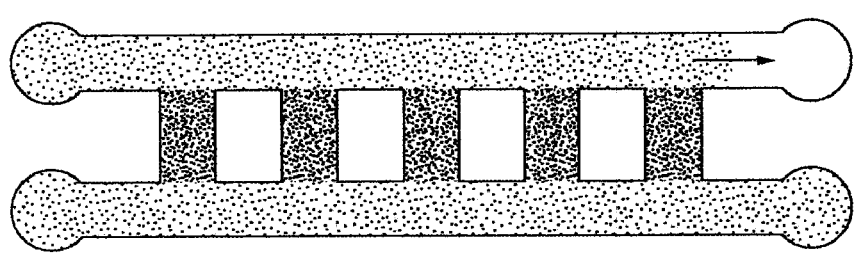
FIG. 3A, FIG. 3B, FIG. 3C, and FIG. 3D consist of diagrams illustrating the method for supplying a reaction solution to a microreactor array in Embodiment 1.
Figure 3C:
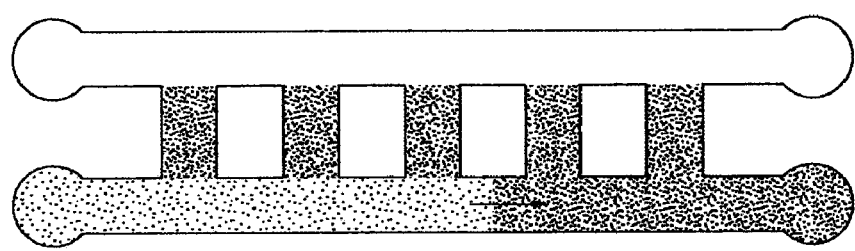
Figure 3B:
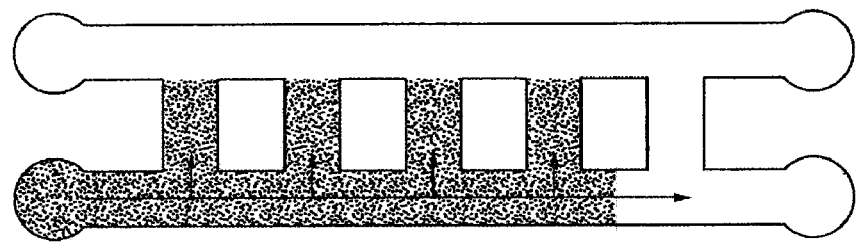
Figure 3A:
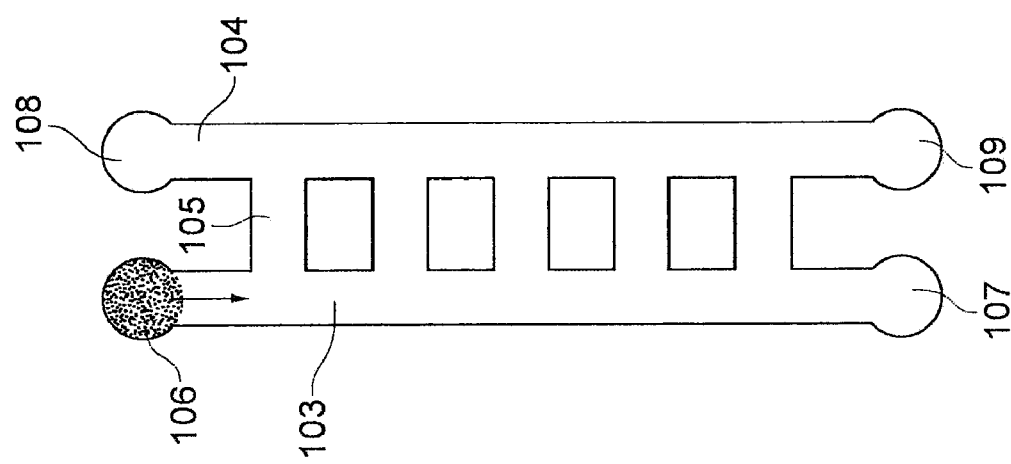

First, as shown in FIG. 3A, when a reaction solution is supplied from the opening 106 to the reaction solution introduction channel 103 using a pipette, a syringe pump, or the like, the reaction solution advances under capillary force while filling the reaction solution introduction channel 103. Then, as shown in FIG. 3B, when the reaction solution reaches the connected portions with the reaction vessels 105, capillary force causes the reaction solution to move into the reaction vessels 105. As discussed above, the relationship a>b>c exists between the width a of the reaction solution introduction channel 103, the width b of the connected portions of the reaction vessels 105 and the reaction solution introduction channel 103, and the depth c of the reaction vessels 105. Accordingly, the capillary force increases in strength from inside the reaction solution introduction channel 103, to the connected portions, to inside the reaction vessels 105, in that order, so the reaction solution advances under capillary force into the reaction vessels 105 and fills the reaction vessels 105.

The reaction solution that has moved into the reaction vessels 105 halts its advance at the connected portions between the reaction vessels 105 and the discharge channel 104. The reason for this is that since the relationship e>d exits between the width d of the connected portions between the reaction vessels 105 and the discharge channel 104 and the width e of the discharge channel 104, the capillary force is smaller inside the discharge channel 104 than in the connected portions, and therefore the reaction solution cannot advance under capillary force from the reaction vessels 105 into the discharge channel 104.

As discussed above, all of the reaction vessels 105 can be filled with the reaction solution by capillary force. The volume of the reaction vessels 105 is approximately 0.04 µL, and the amount of reaction solution with which they are filled is also approximately 0.04 µL. This amount is far less than the 20 µL of reaction solution that was typically used in conventional PCR. In the past a pipette was used to quantify the reaction solution, but a tiny amount of reaction solution as small as 0.04 µL is difficult to quantify with a pipette. With this embodiment, however, even a miniscule amount of reaction solution can be accurately introduced into the reaction vessels 105.

As shown in FIG. 3C, a pipette or a syringe pump is used to inject mineral oil through the opening 106 into the reaction solution introduction channel 103. If reaction solution remains in the reaction solution introduction channel 103 at this point, it is discharged through the opening 107. On the other hand, the reaction solution in the reaction vessels 105 is not discharged to the discharge channel 104, and even if the mineral oil reaches the connected portions with the reaction vessels 105, it will not move into the reaction vessels 105. While the reaction solution introduction channel 103 is being filled with the mineral oil, the two openings 108 and 109 of the discharge channel 104 are preferably blocked off with tape or the like.

As shown in FIG. 3D, a pipette or a syringe pump is used to inject mineral oil through the opening 108 into the discharge channel 104, filling the channel. While the discharge channel 104 is being filled with the mineral oil, the two openings 106 and 107 of the reaction solution introduction channel 103 are preferably blocked off with tape or the like.

Thus filling the reaction solution introduction channel 103 and the discharge channel 104 with mineral oil separates the individual reaction vessels 105 and prevents contamination between the reaction vessels 105. Also, during reaction processing, the inside of the reaction vessels 105 can be prevented from drying out. Instead of mineral oil, any liquid can be used as long as it is immiscible with the reaction solution and evaporates more slowly than the reaction solution.

Once reaction solution has been supplied to the microreactor array 10 by the above procedure, the microreactor array 10 is placed in a thermal cycler and subjected to PCR processing. In general, first a step is performed in which double-stranded DNA is dissociated at 94° C., and then a step is performed in which the primer is annealed at approximately 55° C., and then heat-resistant DNA polymerase is used for complementary chain copying at approximately 72° C., and this cycle is repeated.

Next, a method for carrying out real time PCR using the microreactor array 10 will be described.

When the microreactor array 10 is used as a real time PCR apparatus, the inner walls of the reaction vessels 105 are coated ahead of time with a fluorescent probe and a primer used in PCR, and a CCD sensor or the like is used to measure the fluorescent intensity every cycle. The initial amount of target nucleic acid is calculated from the number of cycles at which a specific fluorescent intensity is reached. The method for carrying out the real time PCR is not limited to the one given above. For example, no fluorescent probe is needed when using a double-strand bonded fluorescent colorant such as SYBR® Green.

Thus, with Embodiment 1, the reaction vessels 105 can be filled with the reaction solution by capillary force, so even when only an extremely small amount of reaction solution is used, which would be difficult to quantify with a pipette, the specified amount can still be supplied to the reaction vessels 105. Also, since only a small amount of reaction solution is needed, the cost can be reduced. Reducing the amount of reaction solution also shortens the reaction time (shortens the PCR cycle time), affording more efficient processing. Also, since processing can be performed in many reaction vessels 105 at once, tests involving many different samples and so forth can be carried out efficiently with a small amount of reagent. Also, each of the reaction devices [sic] 105 can be coated with a fluorescent probe and a primer necessary for quantification and amplification of the target nucleic acid, and this allows the user to perform PCR processing easily merely by filling reaction vessels with the reaction solution.

Also, after the reaction vessels 105 have been filled with reaction solution, PCR processing is performed only after the reaction solution introduction channel 103 and the discharge channel 104 have been filled with mineral oil, so the individual reaction vessels 105 are separated, which prevents contamination between the reaction vessels. Also, the reaction solution in the reaction vessels 105 can be prevented from evaporating during reaction processing.

In Embodiment 1, the microreactor array 10 was used as a real time PCR apparatus, but it can be utilized in many different kinds of reaction involving genes or biological samples. For instance, it can also be used in processing in which the insides of the reaction vessels 105 are coated with an antigen, an antibody, a receptor, an enzyme or other protein, a peptide (oligopeptide), or the like that distinctively complements (such as adsorption or bonding) a specific protein, and the protein of the target is detected from the reaction solution.

What is claimed is:

1. A biological sample reaction method that utilizes a biological micro reaction array, the method comprising the steps of:

supplying a reaction solution through a first opening into a first channel of the array having a capillary force defined as A;

filling a plurality of reaction vessels of the array with the reaction solution, a capillary force of first connected portions between the reaction vessels and the first channel is defined as B and a capillary force of the reaction vessels is defined as C;

filling the first channel and a second channel of the array with a liquid that is both immiscible with the reaction solution and evaporates more slowly than the reaction solution, the first channel is connected to a first end of each of the reaction vessels and the second channel is connected to a second end of each of the reaction vessels, a capillary force of second connected portions between the second channel and the reaction vessels is defined as D, and a capillary force of the second channel is defined as E, wherein $A<B<C<D$ and $E<D$; and performing biological sample reaction processing.

2. The biological sample reaction method according to claim 1, wherein the biological sample reaction processing includes nucleic acid amplification; and wherein the reaction solution includes a target nucleic acid, an enzyme for amplifying a nucleic acid, and a nucleotide at a specific concentration.

3. The method of claim 1, further comprising coating each of the reaction vessels with a reagent necessary for a reaction.

4. The method of claim 1, further comprising filling each of the reaction vessels with only about 0.04 µL of the reaction solution.

5. The method of claim 1, further comprising providing walls of the reaction vessels with a lyophilic surface treatment prior to filling the reaction vessels with the reaction solution.

6. The method of claim 5, further comprising providing walls of the first channel and providing walls of the second channel with a lyophobic surface treatment prior to filling the first channel and the second channel with the liquid.

7. The method of claim 1, wherein the reaction solution includes at least one of a target nucleic acid, a polymerase, or a nucleotide; and wherein the liquid includes mineral oil.

8. The method of claim 7, wherein the target nucleic acid includes DNA extracted from a biological sample including at least one of blood, urine, saliva, cerebrospinal fluid, or cDNA reversed transcripted from extracted RNA.

9. The method of claim 1, wherein the reaction processing includes inserting the micro reaction array in a thermal cycler.

10. The method of claim 9, further comprising subjecting the micro reaction array to PCR processing.

11. The method of claim 10, further comprising coating the reaction vessels with a fluorescent probe, a PCR primer, and a CCD sensor.

* * * * *